United States Patent [19]

Miura et al.

[11] Patent Number: 5,610,036
[45] Date of Patent: Mar. 11, 1997

[54] MUTANT AOX2 PROMOTER, MICROORGANISM CARRYING SAME, METHOD OF PREPARATION THEREOF AND PRODUCTION OF HETEROLOGOUS PROTEIN USING SUCH MICROORGANISM

[75] Inventors: Masami Miura; Yutaka Ishida; Hideyuki Oi; Koji Murakami; Yukimitsu Nakagawa; Haruhide Kawabe, all of Osaka, Japan

[73] Assignee: The Green Cross Corporation, Osaka, Japan

[21] Appl. No.: 288,899

[22] Filed: Aug. 10, 1994

Related U.S. Application Data

[63] Continuation of Ser. No. 858,830, Mar. 27, 1992, abandoned.

[30] Foreign Application Priority Data

Mar. 27, 1991 [JP] Japan .................................. 3-63598
Mar. 27, 1991 [JP] Japan .................................. 3-63599

[51] Int. Cl.⁶ .............................. C07H 21/04; C12N 1/16; C12N 1/19; C12P 21/02
[52] U.S. Cl. .................... 435/71.1; 435/69.1; 435/172.3; 435/254.23; 435/320.1; 536/24.1; 536/23.4; 935/28; 935/69
[58] Field of Search ................... 536/24.1, 23.1, 536/23.4, 23.7; 435/69.1, 71.1, 71.2, 240.1, 254.1, 254.23, 320.1, 172.3; 935/28, 69

[56] References Cited

U.S. PATENT DOCUMENTS 4,882,279  11/1989  Cregg ................................... 435/172.3
4,895,800  1/1990  Tschopp et al. ........................ 435/69.3

FOREIGN PATENT DOCUMENTS 0387928  12/1989  European Pat. Off. .
0344459  12/1989  European Pat. Off. .

OTHER PUBLICATIONS

American Type Culture Collection, Catalogue of Yeasts, 18th Edition, 1990; Jong et al., EDS., ATCC, Maryland. pp. 45–50.
Koutz et al., (1989). Yeast 5(3):167–177.
Watson et al. (1983) in Recombinant DNA: A Short Course W. H. Freeman and Co. N.Y. p. 86.
Silhavy et al. 1984, In Experiments with Gene Fusions, Cold Spring Harbor Laboratory, N.Y. pp. 7–25.
Watson et al., EDS. "Molecular Biology of the Gene", Benjamin Kumminas Publishing Co., Inc., California., 1987, pp. 368–374 and 571–575.

*Primary Examiner*—Brian R. Stanton
*Attorney, Agent, or Firm*—Sughrue, Mion, Zinn, Macpeak & Seas

[57] ABSTRACT

A mutant AOX2 (alcohol oxidase 2) promoter derived from the natural AOX2 promoter by base sequence deletion, insertion, or substitution is disclosed. A microbial strain carrying a gene under the control of such a mutant AOX2 promoter can be obtained by growing in a methanol-containing medium a strain incapable of producing AOX encoded by the AOX1 gene but carrying the AOX2 gene under the control of the natural AOX2 promoter. A heterologous protein may be produced by cultivating the mutant strain with the desired heterologous protein gene incorporated downstream from the mutant AOX2 promoter. A plasmid carrying the mutant AOX2 promoter is also provided.

8 Claims, 8 Drawing Sheets

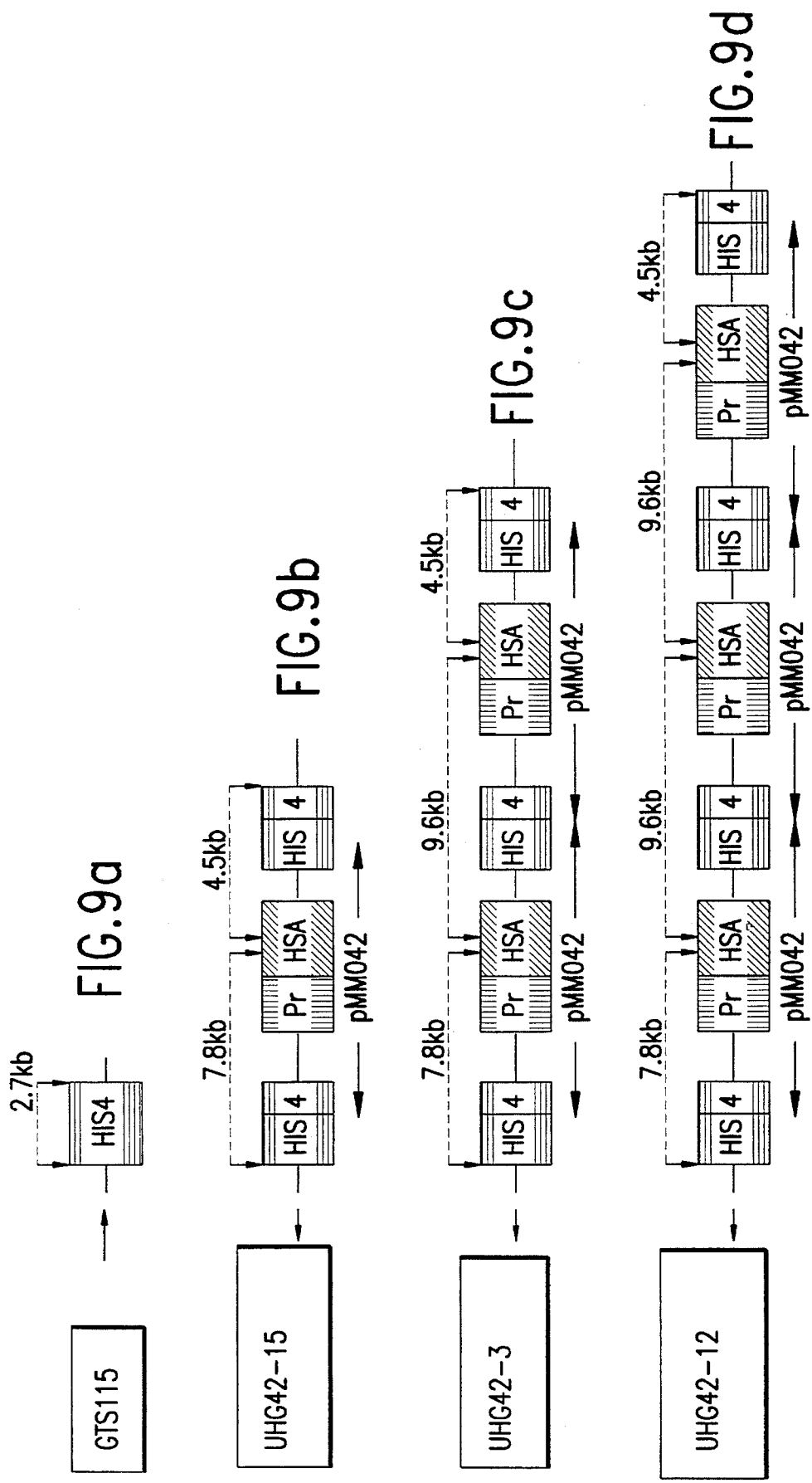

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 1528 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: plasmid DNA ( i x ) FEATURE:
        ( A ) NAME/KEY: promoter
        ( B ) LOCATION: 1

( x i ) SEQUENCE DESCRIPTION: SEQ ID NO:1:

```
AATTCTTTTT   TTCAGACCAT   ATGACCGGTC   CATCTTCTAC   GGGGGGATTA   TCTATGCTTT      60

GACCTCTATC   TTGATTCTTT   TATGATTCAA   ATCACTTTTA   CGTTATTTAT   TACTTACTGG     120

TTATTTACTT   AGCGCCTTTT   CTGAAAAACA   TTTACTAAAA   ATCATACATC   GGCACTCTCA     180

AACACGACAG   ATTGTGATCA   AGAAGCAGAG   ACAATCACCA   CTAAGGTTGC   ACATTTGAGC     240

CAGTAGGCTC   CTAATAGAGG   TTCGATACTT   ATTTTGATAA   TACGACATAT   TGTCTTACCT     300

CTGAATGTGT   CAATACTCTC   TCGTTCTTCG   TCTCGTCAGC   TAAAAATATA   ACACTTCGAG     360

TAAGATACGC   CCAATTGAAG   GCTACGAGAT   ACCAGACTAT   CACTAGTAGA   ACTTTGACAT     420

CTGCTAAAGC   AGATCAAATA   TCCATTTATC   CAGAATCAAT   TACCTTCCTT   TAGCTTGTCG     480

AAGGCATGAA   AAAGCTACAT   GAAAATCCCC   ATCCTTGAAG   TTTTGTCAGC   TTAAAGGACT     540
```

|  |  |  |  |  |  |  |
|---|---|---|---|---|---|---|
| CCATTTCCTA | AAATTTCAAG | CAGTCCTCTC | AACTAAATTT | TTTTCCATTC | CTCTGCACCC | 600 |
| AGCCCTCTTC | ATCAACCGTC | CAGCCTTCTC | AAAAGTCCAA | TGTAAGTAGC | CTGCAAATTC | 660 |
| AGGTTACAAC | CCCTCAATTT | TCCATCCAAG | GGCGATCCTT | ACAAAGTTAA | TATCGAACAG | 720 |
| CAGAGACTAA | GCGAGTCATC | ATCACCACCC | AACGATGGTG | AAAAACTTTA | AGCATAGATT | 780 |
| GATGGAGGGT | GTATGGCACT | TGGCGGCTGC | ATTAGAGTTT | GAAACTATGG | GGTAATACAT | 840 |
| CACATCCGGA | ACTGATCCCA | CTCCGAGATC | ATATGCAAAG | CACGTGATGT | ACCCCGTAAA | 900 |
| CTGCTCGGAT | TATCGTTGCA | ATTCATCGTC | TTAAACAGTA | CAAGAAACTT | TATTCATGGG | 960 |
| TCATTGGACT | CTGATGAGGG | GCACATTTCC | CCAATGATTT | TTTGGGAAAG | AAAGCCGTAA | 1020 |
| GAGGACAGTT | AAGCGAAAGA | GACAAGACAA | CGAACAGCAA | AAGTGACAGC | TGTCAGCTAC | 1080 |
| CTAGTGGACA | GTTGGGAGTT | TCCAATTGGT | TGGTTTTGAA | TTTTACCCA | TGTTGAGTTG | 1140 |
| TCCTTGCTTC | TCCTTGCAAA | CAATGCAAGT | TGATAAGACA | TCACCTTCCA | AGATGAGCTA | 1200 |
| TTTTTGTCGC | ATAAATTTTT | GTCTCGGAGT | GAAAACCCCT | TTTATGTGAA | CAGATTACAG | 1260 |
| AAGCGTCCTA | CCCTTCACCG | GTTGAGATGG | GGAGAAAATT | AAGCGATGAG | GAGACGATTA | 1320 |
| TTGGTATAAA | AGAAGCAACC | AAAATCCCTT | ATTGTCCTTT | TCTGATCAGC | ATCAAAGAAT | 1380 |
| ATTGTCTTAA | AACGGGCTTT | TAACTACATT | GTTCTTACAC | ATTGCAAACC | TCTTCCTTCT | 1440 |
| ATTTCGGATC | AACTGTATTG | ACTACATTGA | TCTTTTTTAA | CGAAGTTTAC | GACTTACTAA | 1500 |
| ATCCCCACAA | ACAAATCAAC | TGAGAAAA |  |  |  | 1528 |

( 2 ) INFORMATION FOR SEQ ID NO:2:

( i ) SEQUENCE CHARACTERISTICS:
        ( A ) LENGTH: 1089 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: plasmid DNA ( i x ) FEATURE:
        ( A ) NAME/KEY: promoter
        ( B ) LOCATION: 1

( x i ) SEQUENCE DESCRIPTION: SEQ ID NO:2:

|  |  |  |  |  |  |  |
|---|---|---|---|---|---|---|
| AATTCTTTTT | TTCAGACCAT | ATGACCGGTC | CATCTTCTAC | GGGGGGATTA | TCTATGCTTT | 60 |
| GACCTCTATC | TTGATTCTTT | TATGATTCAA | ATCACTTTTA | CGTTATTTAT | TACTTACTGG | 120 |
| TTATTTACTT | AGCGCCTTTT | CTGAAAAACA | TTTACTAAAA | ATCATACATC | GGCACTCTCA | 180 |
| AACACGACAG | ATTGTGATCA | AGAAGCAGAG | ACAATCACCA | CTAAGGTTGC | ACATTTGAGC | 240 |
| CAGTAGGCTC | CTAATAGAGG | TTCGATACTT | ATTTTGATAA | TACGACATAT | TGTCTTACCT | 300 |
| CTGAATGTGT | CAATACTCTC | TCGTTCTTCG | TCTCGTCAGC | TAAAATATA | ACACTTCGAG | 360 |
| TAAGATACGC | CCAATTGAAG | GCTACGAGAT | ACCAGACTAT | CACTAGTAGA | ACTTTGACAT | 420 |
| CTGCTAAAGC | AGATCAAATA | TCCATTTATC | CAGAATCAAT | TACCTTCCTT | TAGCTTGTCG | 480 |
| AAGGCATGAA | AAAGCTACAT | GAAAATCCCC | ATCCTTGAAG | TTTTGTCAGC | TTAAAGGACT | 540 |
| CCATTTCCTA | AAATTTCAAG | CAGTCCTCTC | AACTAAATTT | TTTTCCATTC | CTCTGCACCC | 600 |
| AGCCCTCTTC | ATCAACCGTC | CAGCCTTCTC | AAAAGTCCAA | TGTAAGTAGC | CTGCAAATTC | 660 |
| AGGTTACAAC | CCCTCAATTT | TCCATCCAAG | GGCGATCCTT | ACAAAGTTAA | TATCGAACAG | 720 |
| CAGAGACTAA | GCGAGTCATC | ATCACCACCC | AAGATGAGCT | ATTTTGTCG | CATAAATTTT | 780 |
| TGTCTCGGAG | TGAAAACCCC | TTTATGTGA | ACAGATTACA | GAAGCGTCCT | ACCCTTCACC | 840 |

-continued

| | | | | | |
|---|---|---|---|---|---|
| GGTTGAGATG | GGGAGAAAAT | TAAGCGATGA | GGAGACGATT | ATTGGTATAA | AAGAAGCAAC | 900 |
| CAAAATCCCT | TATTGTCCTT | TTCTGATCAG | CATCAAAGAA | TATTGTCTTA | AACGGGCTT | 960 |
| TTAACTACAT | TGTTCTTACA | CATTGCAAAC | CTCTTCCTTC | TATTTCGGAT | CAACTGTATT | 1020 |
| GACTACATTG | ATCTTTTTA | ACGAAGTTTA | CGACTTACTA | AATCCCACA | AACAAATCAA | 1080 |
| CTGAGAAAA | | | | | | 1089 |

( 2 ) INFORMATION FOR SEQ ID NO:3:

( i ) SEQUENCE CHARACTERISTICS:
        ( A ) LENGTH: 1528 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: plasmid DNA ( i x ) FEATURE:
        ( A ) NAME/KEY: promoter
        ( B ) LOCATION: 1

( x i ) SEQUENCE DESCRIPTION: SEQ ID NO:3:

| | | | | | |
|---|---|---|---|---|---|
| AATTCTTTTT | TTCAGACCAT | ATGACCGGTC | CATCTTCTAC | GGGGGGATTA | TCTATGCTTT | 60 |
| GACCTCTATC | TTGATTCTTT | TATGATTCAA | ATCACTTTTA | CGTTATTTAT | TACTTACTGG | 120 |
| TTATTTACTT | AGCGCCTTTT | CTGAAAAACA | TTTACTAAAA | ATCATACATC | GGCACTCTCA | 180 |
| AACACGACAG | ATTGTGATCA | AGAAGCAGAG | ACAATCACCA | CTAAGGTTGC | ACATTTGAGC | 240 |
| CAGTAGGCTC | CTAATAGAGG | TTCGATACTT | ATTTTGATAA | TACGACATAT | TGTCTTACCT | 300 |
| CTGAATGTGT | CAATACTCTC | TCGTTCTTCG | TCTCGTCAGC | TAAAAATATA | ACACTTCGAG | 360 |
| TAAGATACGC | CCAATTGAAG | GCTACGAGAT | ACCAGACTAT | CACTAGTAGA | ACTTTGACAT | 420 |
| CTGCTAAAGC | AGATCAAATA | TCCATTTATC | CAGAATCAAT | TACCTTCCTT | TAGCTTGTCG | 480 |
| AAGGCATGAA | AAAGCTACAT | GAAATCCCC | ATCCTTGAAG | TTTTGTCAGC | TTAAAGGACT | 540 |
| CCATTTCCTA | AAATTTCAAG | CAGTCCTCTC | AACTAAATTT | TTTTCCATTC | CTCTGCACCC | 600 |
| AGCCCTCTTC | ATCAACCGTC | CAGCCTTCTC | AAAAGTCCAA | TGTAAGTAGC | CTGCAAATTC | 660 |
| AGGTTACAAC | CCCTCAATTT | TCCATCCAAG | GGCGATCCTT | ACAAAGTTAA | TATCGAACAG | 720 |
| CAGAGACTAA | GCGAGTCATC | ATCACCACCC | AACGATGGTG | AAAAACTTTA | AGCATAGATT | 780 |
| GATGGAGGGT | GTATGGCACT | TGGCGGCTGC | ATTAGAGTTT | GAAACTATGG | GGTAATACAT | 840 |
| CACATCCGGA | ACTGATCCCA | CTCCGAGATC | ATATGCAAAG | CACGTGATGT | ACCCCGTAAA | 900 |
| CTGCTCGGAT | TATCGTTGCA | ATTCATCGTC | TTAAACAGTA | CAAGAAACTT | TATTCATGGG | 960 |
| TCATTGGACT | CTGATGAGGG | GCACATTTCC | CCAATGATTT | TTTGGGAAAG | AAAGCCGTAA | 1020 |
| GAGGACAGTT | AAGCGAAAGA | GACAAGACAA | CGAACAGCAA | AAGTGACAGC | TGTCAGCTAC | 1080 |
| CTAGTGGACA | GTTGGGAGTT | TCCAATTGGT | TGGTTTTGAA | TTTTACCCA | TGTTGAGTTG | 1140 |
| TCCTTGCTTC | TCCTTGCAAA | CAATGCAAGT | TGATAAGACA | TCACCTTCCA | AGATGAGCTA | 1200 |
| TTTTTGTCGC | ATAAATTTTT | GTCTCGGAGT | GAAAACCCCT | TTATGTGAA | CAGATTACAG | 1260 |
| AAGCGTCCTA | CCCCTCACCG | GTTGAGATGG | GGAGAAAATT | AAGCGATGAG | GAGACGATTA | 1320 |
| TTGGTATAAA | AGAAGCAACC | AAAATCCCTT | ATTGTCCTTT | CTGATCAGC | ATCAAGAAT | 1380 |
| ATTGTCTTAA | AACGGGCTTT | TAACTACATT | GTTCTTACAC | ATTGCAAACC | TCTTCCTTCT | 1440 |
| ATTTCGGATC | AACTGTATTG | ACTACATTGA | TCTTTTTAA | CGAAGTTTAC | GACTTACTAA | 1500 |
| ATCCCCACAA | ACAAATCAAC | TGAGAAAA | | | | 1528 |

( 2 ) INFORMATION FOR SEQ ID NO:4:

( i ) SEQUENCE CHARACTERISTICS:
        ( A ) LENGTH: 1547 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: plasmid DNA ( i x ) FEATURE:
        ( A ) NAME/KEY: promoter
        ( B ) LOCATION: 1

( x i ) SEQUENCE DESCRIPTION: SEQ ID NO:4:

```
AATTCTTTTT  TTCAGACCAT  ATGACCGGTC  CATCTTCTAC  GGGGGGATTA  TCTATGCTTT    60
GACCTCTATC  TTGATTCTTT  TATGATTCAA  ATCACTTTTA  CGTTATTTAT  TACTTACTGG   120
TTATTTACTT  AGCGCCTTTT  CTGAAAAACA  TTTACTAAAA  ATCATACATC  GGCACTCTCA   180
AACACGACAG  ATTGTGATCA  AGAAGCAGAG  ACAATCACCA  CTAAGGTTGC  ACATTTGAGC   240
CAGTAGGCTC  CTAATAGAGG  TTCGATACTT  ATTTTGATAA  TACGACATAT  TGTCTTACCT   300
CTGAATGTGT  CAATACTCTC  TCGTTCTTCG  TCTCGTCAGC  TAAAAATATA  ACACTTCGAG   360
TAAGATACGC  CCAATTGAAG  GCTACGAGAT  ACCAGACTAT  CACTAGTAGA  ACTTTGACAT   420
CTGCTAAAGC  AGATCAAATA  TCCATTTATC  CAGAATCAAT  TACCTTCCTT  TAGCTTGTCG   480
AAGGCATGAA  AAAGCTACAT  GAAAATCCCC  ATCCTTGAAG  TTTTGTCAGC  TTAAAGGACT   540
CCATTTCCTA  AAATTTCAAG  CAGTCCTCTC  AACTAAATTT  TTTTCCATTC  CTCTGCACCC   600
AGCCCTCTTC  ATCAACCGTC  CAGCCTTCTC  AAAAGTCCAA  TGTAAGTAGC  CTGCAAATTC   660
AGGTTACAAC  CCCTCAATTT  TCCATCCAAG  GGCGATCCTT  ACAAAGTTAA  TATCGAACAG   720
CAGAGACTAA  GCGAGTCATC  ATCACCACCC  AACGATGGTG  AAAAACTTTA  AGCATAGATT   780
GATGGAGGGT  GTATGGCACT  TGGCGGCTGC  ATTAGAGTTT  GAAACTATGG  GGTAATACAT   840
CACATCCGGA  ACTGATCCCA  CTCCGAGATC  ATATGCAAAG  CACGTGATGT  ACCCCGTAAA   900
CTGCTCGGAT  TATCGTTGCA  ATTCATCGTC  TTAAACAGTA  CAAGAAACTT  TATTCATGGG   960
TCATTGGACT  CTGATGAGGG  GCACATTTCC  CCAATGATTT  TTTGGGAAAG  AAAGCCGTAA  1020
GAGGACAGTT  AAGCGAAAGA  GACAAGACAA  CGAACAGCAA  AAGTGACAGC  TGTCAGCTAC  1080
CTAGTGGACA  GTTGGGAGTT  TCCAATTGGT  TGGTTTTGAA  TTTTTACCCA  TGTTGAGTTG  1140
TCCTTGCTTC  TCCTTGCAAA  CAATGCAAGT  TGATAAGACA  TCACCTTCCA  AGATGAGCTA  1200
TTTTTGTCGC  ATAAATTTTT  GTCTCGGAGT  GAAAACCCCT  TTTATGTGAA  CAGATTACAG  1260
AAGCGTCCTA  CCCTTCACCG  GTTGAGATGG  GGAGAAAATT  AAGCGATGAG  GAGAAAATTA  1320
AGCGATGAGG  AGACGATTAT  TGGTATAAAA  GAAGCAACCA  AAATCCCTTA  TTGTCCTTTT  1380
CTGATCAGCA  TCAAAGAATA  TTGTCTTAAA  ACGGGCTTTT  AACTACATTG  TTCTTACACA  1440
TTGCAAACCT  CTTCCTTCTA  TTTCGGATCA  ACTGTATTGA  CTACATTGAT  CTTTTTTAAC  1500
GAAGTTTACG  ACTTACTAAA  TCCCCACAAA  CAAATCAACT  GAGAAAA                 1547
```

( 2 ) INFORMATION FOR SEQ ID NO:5:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: other nucleic acid (A) DESCRIPTION: synthetic DNA (ix) FEATURE:
    (A) NAME/KEY: primer_bind
    (B) LOCATION: 1

(xi) SEQUENCE DESCRIPTION: SEQ ID NO:5:

CCGAATTCGA CAATATTCTT TGATGC      26

(2) INFORMATION FOR SEQ ID NO:6:

(i) SEQUENCE CHARACTERISTICS:
    (A) LENGTH: 26 base pairs
    (B) TYPE: nucleic acid
    (C) STRANDEDNESS: single
    (D) TOPOLOGY: linear (ii) MOLECULE TYPE: other nucleic acid
    (A) DESCRIPTION: synthetic DNA (ix) FEATURE:
    (A) NAME/KEY: primer_bind
    (B) LOCATION: 1

(xi) SEQUENCE DESCRIPTION: SEQ ID NO:6:

CCGGATCCAC TAAGCGAGTC ATCATC      26

(2) INFORMATION FOR SEQ ID NO:7:

(i) SEQUENCE CHARACTERISTICS:
    (A) LENGTH: 19 base pairs
    (B) TYPE: nucleic acid
    (C) STRANDEDNESS: double
    (D) TOPOLOGY: linear (ii) MOLECULE TYPE: other nucleic acid
    (A) DESCRIPTION: additional DNA (ix) FEATURE:
    (A) NAME/KEY: insertion_seq
    (B) LOCATION: 1

(xi) SEQUENCE DESCRIPTION: SEQ ID NO:7:

AAATTAAGCG ATGAGGAGA      19

MUTANT AOX2 PROMOTER, MICROORGANISM CARRYING SAME, METHOD OF PREPARATION THEREOF AND PRODUCTION OF HETEROLOGOUS PROTEIN USING SUCH MICROORGANISM

This is a Continuation of application Ser. No. 07/858,830 filed 27 March 1992, now abandoned.

FIELD OF THE INVENTION

The invention relates to a mutant AOX2 promoter, a microorganism carrying said promoter, a method of preparing the same and a method of producing a heterologous protein using said microorganism. The invention further relates to a plasmid containing said mutant AOX2 promoter, a transformant carrying said plasmid and a method of producing a heterologous protein using said transformant.

BACKGROUND OF THE INVENTION

Methanol-utilizing yeasts use methanol as a carbon and energy source. The methanol utilization pathway begins with the oxidation of methanol to formaldehyde. That oxidation step is catalyzed by the enzyme alcohol oxidase (AOX, EC 1.1.3.13). While AOX is expressed at low levels in glucose-containing media, AOX accounts for 30% of solubilized intracellular proteins in methanol-containing media.

*Pichia pastoris*, a methanol-utilizing yeast, carries two AOX genes (the AOX1 gene and the AOX2 gene).

The AOX1 promoter and AOX2 promoter differ markedly in activity. AOX activity in *Pichia pastoris* is due mostly to expression at the AOX1 locus [Molecular and Cellular Biology, 9, 1316 (1989)]. Strains of *Pichia pastoris* in which a heterologous gene is substituted at the AOX1 locus grow slowly in methanol-containing media, theyby requiring a lengthy cultivation period, because the methanol utilization is based on AOX2 activity alone.

Among the two AOX genes coding for AOX, the AOX1 promoter, which is the regulatory region of the AOX1 gene, has high activity and can be used for the expression of heterologous proteins in high yields in methanol-utilizing yeasts. However, the AOX2 promoter is weak in activity and hence unsuitable for the expression of heterologous proteins.

Recently, studies have been conducted to produce heterologous proteins using the regulatory region of said AOX gene [e.g. EP-A-344459 (JP-A-2-104290) (the term "JP-A" used herein means an unexamined published Japanese patent application.); EP-A-343388 (JP-A-2-242694); GB-A-2217332 (JP-A2-303497)].

Natural AOX2 promoter is described in U.S. Pat. No. 5,032,516.

Once a gene coding for a heterologous protein has been inserted by substitution into the AOX1 gene region of the host, methanol utilization must depend solely on AOX2 activity. The growth rate of such mutants in methanol-containing media is inferior to that of the wild-type host which in return disadvantageously makes it necessary to employ a prolonged cultivation period.

It is an object of the invention to provide a yeast strain capable of good growth in methanol-containing media in contrast to other yeast strains lacking AOX1 gene activity and capable of expressing a heterologous protein, as well as a method of obtaining such a strain.

Another object of the invention is to provide a novel promoter for high-level expression of a heterologous protein, as well as a method of obtaining such promoter.

A further object is to provide a transformant comprising a plasmid containing said promoter and thereby establishing a heterologous protein production system.

SUMMARY OF THE INVENTION

The above objects can be accomplished by providing:

(1) a mutant AOX2 promoter derived from the wild-type AOX2 promoter by partial deletion or substitution in the base sequence thereof or addition of a novel base sequence thereto;

(2) a microbial strain carrying, on the chromosome thereof, the AOX gene under the control of the mutant AOX2 promoter mentioned in (1) above;

(3) a method of obtaining the strain mentioned in (2) above which comprises cultivating a strain in which the AOX2 gene is under the control of the wild-type AOX2 promoter in a methanol-containing medium to thereby cause a mutation in the wild-type AOX2 promoter;

(4) a method of producing a heterologous protein which comprises cultivating the strain mentioned in (2) above;

(5) a plasmid containing the mutant AOX2 promoter mentioned in (1) above;

(6) a transformant obtained by introduction of the plasmid mentioned in (5) above; and (7) a method of producing a heterologous protein which comprises cultivating the transformant mentioned in (6) above.

BRIEF DESCRIPTION OF THE DRAWINGS

In FIG. 1, "Prom" means promoter, "t" means terminator and "polyA" means poly A region.

In FIG. 5, "BAP" means bacterial alkaline phosphatase and "AOX2 prom" means AOX2 promoter.

In FIG. 7, "p" means promoter and "t" means terminator.

FIG. 9 illustrates the procedure of Example 7. In FIG. 9, "■" means probe (0.6 kb KpnI fragment), "Pr" means AOX2 promoter and "↓" means BglII cleavage site.

DETAILED DESCRIPTION OF THE INVENTION

(1) Mutant AOX2 Promoter

Figure 1:
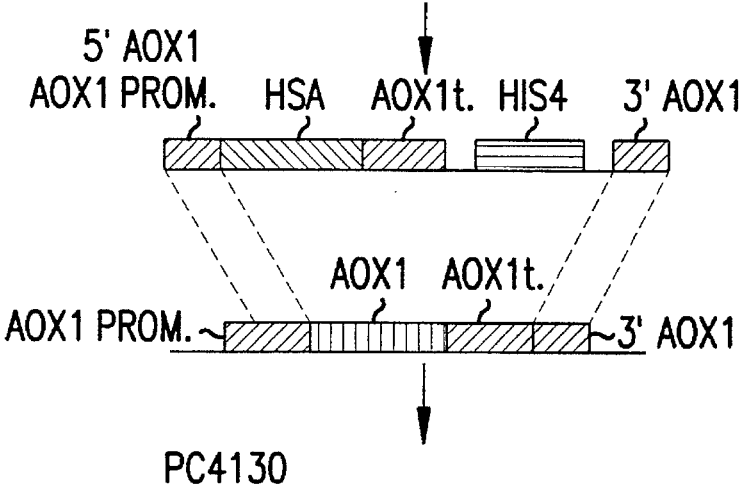
FIG. 1 illustrates a construction scheme for PC4130 and a method of obtaining GCP101.
Figure 1:
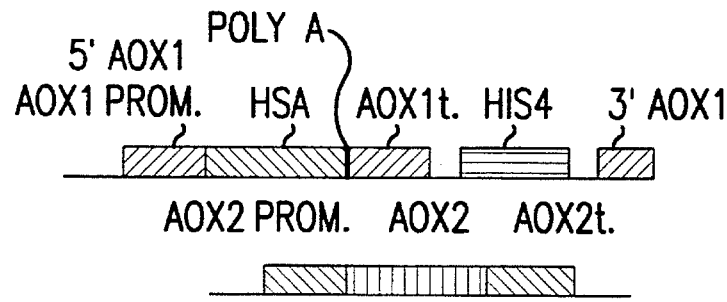

The mutant AOX2 promoter of the invention is derived from the natural, i.e. wild-type, AOX2 promoter by partial deletion or substitution in the base sequence thereof or addition of a novel base sequence thereto.

a. Partial Deletion in the Base Sequence of the Wild-Type AOX2 Promoter

The site of deletion is not critical provided that it is within the wild-type AOX2 promoter region. For instance, it may be between base No. 730 and base No. 1528 of the base sequence containing the wild-type AOX2 promoter as shown under SEQ ID NO: 1. The deletion may involve one or more bases and may occur at one or more loci. As a particular example, there may be mentioned the promoter specifically shown under SEQ ID NO: 2 in which the 439 base pairs from base No. 749 (C) to base No. 1187 (T) of the sequence under SEQ ID NO: 1 are deleted.

b. Partial Substitution in the Base Sequence of the Wild-Type AOX2 Promoter

The substitution site is not critical provided that it is within the wild-type AOX2 promoter region. For instance, it may be between base No. 730 and base No. 1528 of the AOX2 promoter-containing base sequence shown under SEQ ID NO: 1. The substitution may involve one or more bases and may occur at one or more loci. As a particular example, there may be mentioned the promoter specifically shown under SEQ ID NO: 3 in which the base at site No. 1274 (T) of the base sequence shown under SEQ ID NO: 1 has been replaced by C.

c. Addition of a New Base Sequence to the Wild-Type AOX2 Promoter

The addition site is not critical provided that it is within the wild-type AOX2 promoter region. For instance, it may be between base No. 730 and base No. 1528 of the wild-type AOX2 promoter-containing base sequence shown under SEQ ID NO:1. The addition may involve one or more bases and may occur at one or more loci. As a particular example, there may be mentioned the promoter specifically shown under SEQ ID NO: 4 which has an additional sequence shown under SEQ ID NO: 7 between base No. 1314 (A) and base No. 1315 (C) of the base sequence shown under SEQ ID NO: 1.

In the above-mentioned base sequences respectively shown under SEQ ID NO: 2, 3 and 4, the region from base No. 1 to base No. 730, for instance, is given as the same sequence as that of the wild type, for simplicity's sake. It is obvious, however, that the region of bases 1–730 is not limited to that shown but may include deletions, substitutions and/or insertions where appropriate.

The deletion, substitution or addition in the base sequence of the wild-type AOX promoter can be effected using those genetic engineering techniques that are in general use, such as site-directed deletion [Nucl. Acids Res., 11, 164 (1983)], site-directed mutagenesis and use of a synthetic gene in combination with restriction enzyme treatment.

(2) Microbial Strain Carrying, on the Chromosome Thereof, a Mutant AOX2 Promoter The microbial strain of the invention carries, on its chromosome, the AOX gene under the control of the mutant AOX2 promoter mentioned in (1) above.

More particularly, said strain carries the AOX gene under the control of the mutant AOX2 promoter mentioned in (1) above in the chromosome, without the production of AOX1 gene-encoded AOX. More specifically, the strain has, on its chromosome, the AOX1 promoter and the mutant AOX2 promoter mentioned in (1) above, with a heterologous protein gene being under the control of the AOX1 promoter and the AOX gene under the control of the mutant AOX2 promoter.

As such microbial strains, there may be mentioned the strains GCP101 and SHG4105-4.

(3) Method of Obtaining a Microbial Strain Carrying, on Its Chromosome, a Mutant AOX2 Promoter 1) Starting Microbial Strain The starting microbial strain to be used in the practice of the invention carries, on its chromosome, the AOX2 gene under the control of the wild-type AOX2 promoter. Thus, the strain carries, on its chromosome, the AOX1 promoter and AOX2 promoter, with the AOX1 gene under the control of the AOX1 promoter and the AOX2 gene under the control of the AOX2 promoter.

Such a microbial strain is, for example, *Pichia pastoris* (wild type) and, as a particular example, there may be mentioned the strain GTS115 [NRRL deposit No. Y-15851; Gene, 5.9, 115–125 (1987)].

2) Introduction of a Heterologous Protein Gene

A heterologous protein gene is introduced into the starting strain mentioned in 1) above to cause thereby substitution with the heterologous protein gene in the AOX1 gene region.

As the heterologous protein, there may be mentioned human serum albumin (HSA), hepatitis B virus antigen, urokinase and interferons, among others.

As described in EP-A-344459 (JP-A-2-104290), a linear, integration site-specific vector having a heterologous protein gene transcription unit and a marker or the like between the 5' and 3' homologous regions of the AOX1 gene is used to substitute the AOX1 gene (cf. FIG. 1). The transformation of the starting strain is performed by a per se known method.

As specific examples of such strains, there may be mentioned PC4130 and PC4105.

A heterologous protein gene is inserted into the AOX1 gene region, or the AOX1 gene is subjected to partial modification (deletion, substitution or addition, for example) so that AOX production by the AOX1 gene is diminished followed by mutation in that condition and by the subsequent introduction of a heterologous protein gene.

3) Obtainment of Transformants

The strain (transformant in which AOX1 production by the AOX1 gene no longer occurs) mentioned in 2) above is cultured in a methanol-containing medium to cause thereby mutation in the AOX2 promoter region.

The methanol concentration is, for example, about 1 to 5%. The medium may be a natural one or an artificial one. As the natural medium, there may be mentioned YP medium (1% yeast extract +2% polypeptone), for instance. The cultivation is generally carried out at 15° to 43° C. (suitably at about 30° C.) for about 20 to 120 hours, if necessary with aeration and/or stirring. After completion of the cultivation, a part or the whole of the culture is taken and transferred to a fresh, methanol-containing medium and cultivation is continued. On the occasion of subculture, a part of the culture is taken and diluted and the dilution is spread on a nutrient-poor, methanol-containing plate, for example a 2% MeOH-YNB w/o a.a. plate (0.7% yeast nitrogen base without amino acids, 2% methanol and 1.5% agar powder), followed by incubation at 30° C. Transformants can be obtained from colonies resulting after about 3 to 14 days of incubation.

4) Recovery of the Mutant AOX2 Promoter

The mutant AOX2 promoter can be recovered from the transformant mentioned in 2) above by cloning from the AOX2 promoter region using appropriate genetic engineering techniques.

The base sequence of the promoter recovered can be analyzed by a per se known technique.

(4) Method of Producing a Heterologous Protein Using the Microbial Strain Mentioned in (2) Above The strain (transformant) mentioned in (2) above is cultured in a medium per se known for the host cells. The medium preferably should contain methanol. The methanol concentration is, for example, about 0.01 to 5%. The medium may be a natural one or an artificial one. The natural medium includes, among others, YNB medium (0.7% yeast nitrogen base) and YP medium (1% yeast extract +2% polypeptone).

The cultivation generally is carried out at 15° to 43° C. (preferably about 30° C.) for about 20 to 360 hours, if necessary with aeration and/or stirring.

After cultivation, the culture supernatant is recovered and the heterologous protein can be purified therefrom by a per se known method, for example by affinity chromatography or gel filtration fractionation.

(4) Plasmid

The plasmid of the invention carries the mutant AOX2 promoter mentioned in (1) above.

The plasmid of the invention may contain a signal peptide gene, structural protein gene, terminator, homologous region, marker gene, autonomously replicating sequence replicable in the host and so forth.

Usable as a signal peptide gene are human serum albumin prepro peptide gene or modified gene thereof (EP-319641 (JP-A-2-167095)), yeast invertase signal peptide gene, yeast α-factor signal peptide gene and artificially synthesized leader sequence (EP-329127 (JP-A-1-240191)).

Examples of autonomously replicating sequences are PARS1 and PARS2 isolated from *Pichia pastoris* chromosome DNA (U.S. Pat. No. 4,837,148).

As the structural gene, there may be mentioned, among others, heterologous protein (e.g. human serum albumin, prourokinase, tissue plasminogen activator, hepatitis B surface antigen, various interferons etc.) genes, the AOX1 gene and the AOX2 gene.

As examples of the terminator, there may be mentioned the AOX1 terminator and the AOX2 terminator.

The homologous region includes, among others, HIS4, URA3, LEU2 and ARG4.

Usable as the marker gene are antibiotic resistance genes and auxotrophic mutation-complementing genes, for instance. As the antibiotic, there may be mentioned cycloheximide, G-418, chloramphenicol, bleomycin and hygromycin, among others. The auxotrophic mutation-complementing genes include, among others, HIS4, URA3, LEU2 and ARG4.

The transcriptional unit includes, in the 5' to 3' direction at least the mutant AOX2 promoter, a signal peptide gene, a structural protein gene and a terminator, operably linked in that order.

The plasmid of the invention can be prepared using generally accepted genetic engineering techniques.

(5) Transformant

The transformant of the invention contains the plasmid mentioned in (4) above introduced thereinto.

A yeast is preferred as the host in the practice of the invention. More preferred is *Pichia pastoris*. As a particular example, there may be mentioned the strain GTS115 (NRRL deposit No. Y-15851).

Host (yeast) cells can be transformed by a per se known method, for example the calcium phosphate precipitation method, the protoplast fusion method using polyethylene oxide or the electroporation method. Desired transformants then are selected.

The plasmid may occur in the host cells in the form of an insert in the chromosome, in the form integrated in the chromosome by recombination or in the plasmid form.

The number of copies of a foreign gene as introduced into the host may be one or more.

One and the same strain may contain the plasmid of the invention together with another plasmid for the expression of a heterologous gene under the control of another promoter.

(6) Method of Heterologous Protein Production Using the Transformant Mentioned in (5) Above Heterologous proteins can be produced in the same manner as mentioned in (2) above by cultivating the transformant obtained as mentioned in (5) above.

The following working examples and test examples further illustrate the present invention. They are, however, by no means limitative of the scope of the invention.

The techniques, reaction procedures and analytical methods used in the practice of the invention are well known in the art. Unless otherwise indicated, all enzymes are available from commercial sources, for example from Takara Shuzo.

Unless otherwise specified, the buffers and reaction conditions used for enzymatic reactions were those recommended by suppliers of the enzymes.

The yeast strains *Pichia pastoris* GTS115, PC4130 and PC4105 and the plasmids pPGP1 and pPGS1 are in the possession of the inventors.

The transformation of *Escherichia coli* with plasmids, plaque hybridization and electrophoresis were carried out as described in "Molecular Cloning", Cold Spring Harbor Laboratory, 1982.

EXAMPLE 1 Obtainment of GCP101 (cf. FIG. 1)

The strain PC4130 was obtained by substituting a fragment resulting from NotI cleavage of the plasmid pPGP1 having a transcriptional unit for HSA expression under the control of the AOX1 promoter for the AOX1 gene region of *Pichia pastoris* GTS115 (his4) by the method described in EP-A-344459 (JP-A-2-104290). The strain lacks the AOX1-structural gene so that the growth rate of the yeast in a medium containing methanol as the carbon source is low (Mut⁻strain).

PC4130 was inoculated into 3 ml of YPD medium (1% yeast extract, 2% Bacto-peptone and 2% glucose). After 24 hours of incubation, the cultured cells were inoculated into 50 ml of 2% MeOH-YP medium (1% yeast extract, 2% Bacto-peptone and 2% methanol) to an initial optical density at 540 nm ($OD_{540}$) of 1. After 3 days of cultivation at 30° C., the culture was inoculated into 50 ml of 2% MeOH-YP medium to an initial $OD_{540}$ of 1. The same subculturing procedure was repeated at 3-day intervals. On the occasion of each passage, the cell suspension was diluted with sterile water to a concentration of $10^7$ cells/plate for spreading on 2% MeOH-YNB w/o a.a. plates (0.7% yeast nitrogen base without amino acids, 2% methanol and 1.5% agar), followed by 5 days of incubation at 30° C. and the subsequent checking for the presence or absence of colonies. A 2% MeOH-YNB w/o a.a. plate spread with cells obtained after 12 days of subculture gave 20 colonies. (On that kind of plate, a Mut⁻ strain hardly grows while a Mut⁺ strain proliferates.) The colony formation on said plate thus indicates that a Mut⁺ mutant with an increased capacity to utilize methanol was obtained. One of the colonies obtained was diluted appropriately with sterile water and the dilution was spread over a 2% MeOH-YNB w/o a.a. plate for the formation of isolated single colonies. One of those was designated as GCP101.

Comparison was made between PC4130 and GCP101 with respect to the growth rates on various media. One loopful of cells stored at 4° C. on a YNB w/o a.a. plate (0.7% yeast nitrogen base without amino acids, 2% glucose and 1.5% agar powder) was inoculated into 3 ml of YPD medium in each test tube and cultured at 30° C. for 24 hours. Cells then were inoculated into a flask containing 50 ml of each medium to an initial $OD_{540}$ of 0.1 and cultured at 30° C. The cell proliferation degree and the human serum albumin concentration in the culture supernatant were determined at 24-hour intervals (Table 1). The human serum albumin concentration was determined by the RPHA method (European Patent No. 122620). The media used were YPD medium, 2% MeOH-YP medium (1% yeast extract, 2% Bacto-peptone and 2% methanol) and 4% MeOH-YP medium (1% yeast extract, 2% Bacto-peptone and 4% methanol).

While no significant difference was observed between the two strains in the medium containing glucose as the carbon source, GCP101 showed increased growth (transformation to Mut⁺) in the media containing methanol as the carbon source as compared with PC4130. As for HSA production, there was little difference between GCP101 and PC4130.

TABLE 1

Comparison between GCP101 and PC4130 with respect to cell proliferation and HSA production in different media

| Medium | Strain | Cultivation period (hours) | | | |
|---|---|---|---|---|---|
| | | 0 | 24 | 48 | 72 |
| YPD | PC4130 | 0.1 | 67 | 80 | 78 |
| | PC4130 | | — | — | — |
| | GCP101 | 0.1 | 63 | 78 | 79 |
| | GCP101 | | — | — | — |
| 2% MeOH—YP | PC4130 | 0.1 | 16 | 36 | 46 |
| | PC4130 | | 10 | 60 | 100 |
| | GCP101 | 0.1 | 24 | 63 | 63 |
| | GCP101 | | 10 | 70 | 80 |
| 4% MeOH—YP | PC4130 | 0.1 | 9 | 20 | 28 |
| | PC4130 | | 1 | 30 | 80 |
| | GCP101 | 0.1 | 10 | 57 | 84 |
| | GCP101 | | 2 | 60 | 120 |

Notes:
Upper row: proliferation degree ($OD_{540}$);
lower row: HSA production (mg/l);
—: not detected for each medium and for each strain.

EXAMPLE 2 Cloning of the AOX2 Gene

Figure 2:
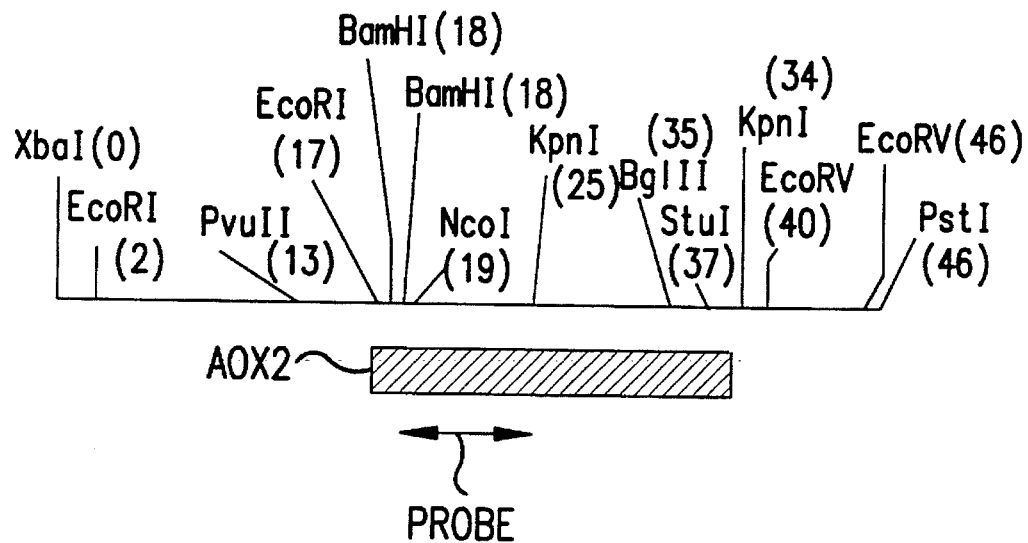
FIG. 2 depicts a restriction enzyme map of the vicinity of the AOX2 gene. The numbers in parentheses respectively indicate the distances (×100 bases) from the XbaI site (distance 0).

The sequence and restriction enzyme map of the AOX2 gene and its vicinity have been reported by Cregg et al. [Mol. Cell. Biol., 9, 1316–1323 (1989)] and Koutz et al. [Yeast, 5, 167–177 (1989)]. Therefore a plan was made to clone the AOX2 gene with reference to those reports. The restriction enzyme map of the AOX2 gene and its vicinity is shown in FIG. 2.

First, the chromosomal DNA's were extracted and purified from both of strains PC4130 and GCP101 by the method of Cameron et al. [Nucleic Acids Res., 4, 1429 (1977)]. Each chromosomal DNA was subjected to complete digestion with XbaI and PstI to give a fragment fully covering the AOX2 promoter region, AOX2 structural gene and AOX2 terminator. The digest was collected by ethanol precipitation and centrifugation, dried, and dissolved in sterile water. EcoRI methylase (Takara Shuzo) was added and the solution was incubated. The reaction mixture was extracted with TE-saturated phenol-chloroform, then with chloroform and the aqueous layer was subjected to ethanol precipitation. The precipitate was collected by centrifugation, dried, and dissolved in sterile water.

The termini were blunted using a DNA blunting kit (Takara Shuzo), and an EcoRI linker, d(pG-G-A-A-T-T-C-C) (Takara Shuzo) was ligated thereto using a DNA ligation kit (Takara Shuzo). Again, precipitation was effected with ethanol, the precipitate was recovered by centrifugation, dried and dissolved in sterile water. EcoRI was added and incubation was carried out at 37° C. for 1 hour. Electrophoresis was performed on a 1% agarose gel and a gel region corresponding to 4–5 kb was excised.

Following electroelution of the gel region and purification using GENE CLEAN II (BI0101) for DNA recovery, the recovered DNA was dissolved in sterile water and ligated to λgt10 arms (Protoclone™ System; Promega) and in vitro packaging was carried out using Gigapack GOLD3 (Stratagene). The resulting mixture was exposed to *E. coli* C600 and C600hfl strains adjusted to $A_{600}=2$. Cells of each strain were sowed onto an NZY plate (1% NZ amine, 0.5% sodium chloride, 0.5% yeast extract, 0.02% magnesium sulfate and 1.5% agar powder) for library formation, followed by titer assaying. Recombinant phage was adsorbed on *E. coli* C600hfl cells and the cells were sowed onto NZY plates to give about 500 plaques on each plate.

For the transformants derived from each of the PC4130 and GC101 strains, four nylon membranes (Colony/Plaque Screen™, NEN) were used. Cells were transferred to the membranes and subjected to denaturation, neutralization and fixation treatments. The probe used, an EcoRV-BglII fragment corresponding to the first half of the *Pichia pastoris* IFO 1013-derived AOX1 structural gene, was prepared by labeling with $^{33}P$ using a random primer labeling kit (Takara Shuzo). Prehybridization was performed in a solution containing 1% BSA, 1 mM EDTA, 0.5M $NaH_2PO_4$ (pH 7.2) and 7% SDS at 65° C. for 5 minutes. Hybridization was carried out in a $^{32}P$-probe solution containing 1% BSA, 1 mM EDTA, 0.5M $NaH_2PO_4$ (pH 7.2) and 7% SDS overnight at 65° C. For washing, the cells were incubated in 0.5M $NaH_2PO_4$ (pH 7.2) at room temperature for 10 minutes and then incubated in a solution containing 0.5% BSA, 1 mM EDTA, 40 mM $NaH_2PO_4$ (pH 7.2) and 5% SDS at 37° C. for 30 minutes. The latter incubation was repeated three times in all. The filters were air-dried and allowed to stand each in contact with an X-ray film in an X-ray exposure cassette at −80° C. for 16 hours for autoradiography.

From each strain, two positive clones were obtained. With one clone for each strain, phage proliferation was effected and the phage DNA was extracted. The DNA's thus obtained were cleaved with EcoRI and the formation of the desired fragments (1.5 kb and 2.9 kb) was confirmed by agarose gel electrophoresis. pUC19 (Bethesda Research Laboratories) was cleaved with EcoRI, treated with alkaline phosphatase and the resultant fragment was recovered and ligated to the EcoRI digest of the phage DNA.

The ligation mixture was used to transform *E. coli* HB101. The cells were sowed onto L plates containing 40 µg/ml of ampicillin (as prepared by dissolving 0.62 g of Tris base, 10 g of polypeptone, 5 g of yeast extract and 5 g of sodium chloride in water, adding water to make 1 liter, adding 15 g of agar powder, autoclaving the mixture, adding ampicillin after cooling, distributing the same into plastic dishes and allowing the same to solidify, and cultured overnight at 37° C.

For each of the resultant colonies, a miniprep was performed and the plasmid was extracted and subjected to screening by EcoRI digestion. As a result, clones with the 1.5-kb and 2.9-kb fragments respectively inserted in pUC19 were obtained for both the strains PC4130 and GCP101. The clones were shake-cultured overnight at 37° C. in super broth containing 40 µg/ml of ampicillin (prepared by dissolving 12 g of Bacto-tryptone, 24 g of yeast extract and 5 ml of glycerol in water, adding water to make 900 ml, autoclaving the solution (solution A) and mixing solution A with solution B prepared by dissolving 3.81 g of potassium dihydrogen phosphate and 12.5 g of dipotassium hydrogen phosphate in water and adding water to make 100 ml, in a volume/volume ratio of 9:1) and the plasmid DNA's were extracted and purified in large quantities by the alkaline-SDS method.

Figure 3:
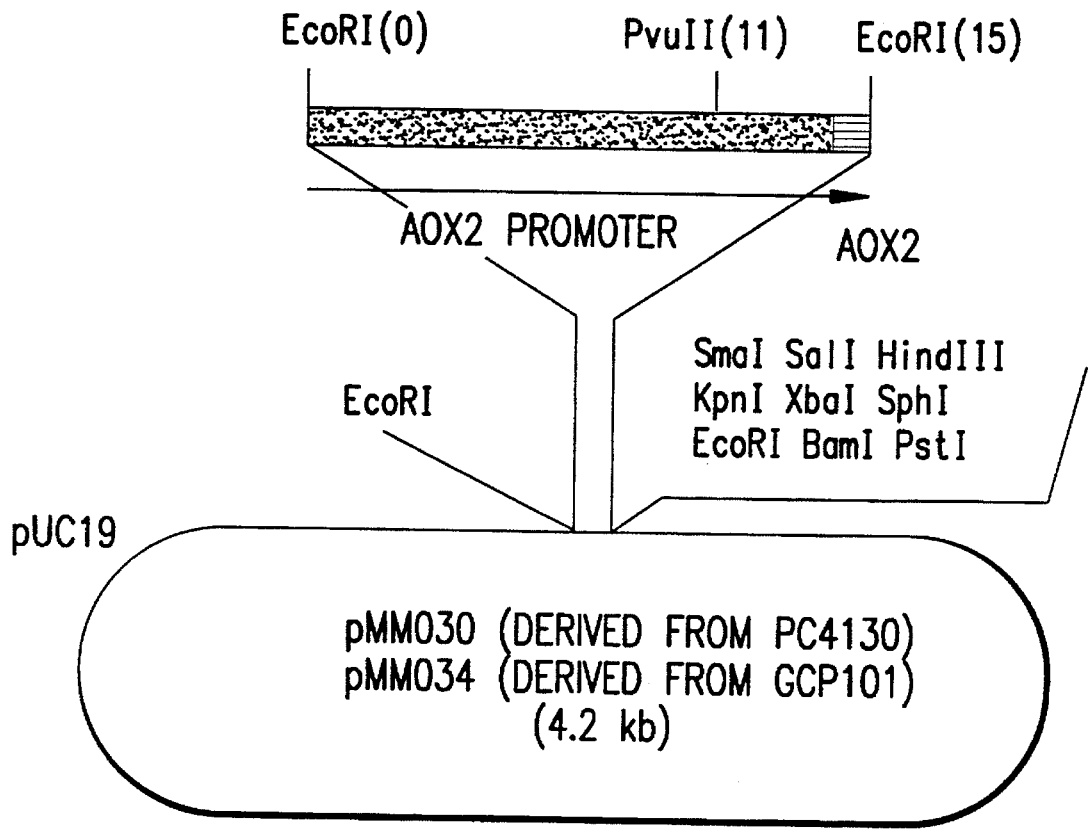
FIG. 3 depicts plasmids pMM030 and pMM034 in which the AOX2 promoter has been cloned, each with a restriction enzyme map. The numbers in parentheses respectively indicate the distances (×100 bases) from the EcoRI site (distance 0).
Figure 4:
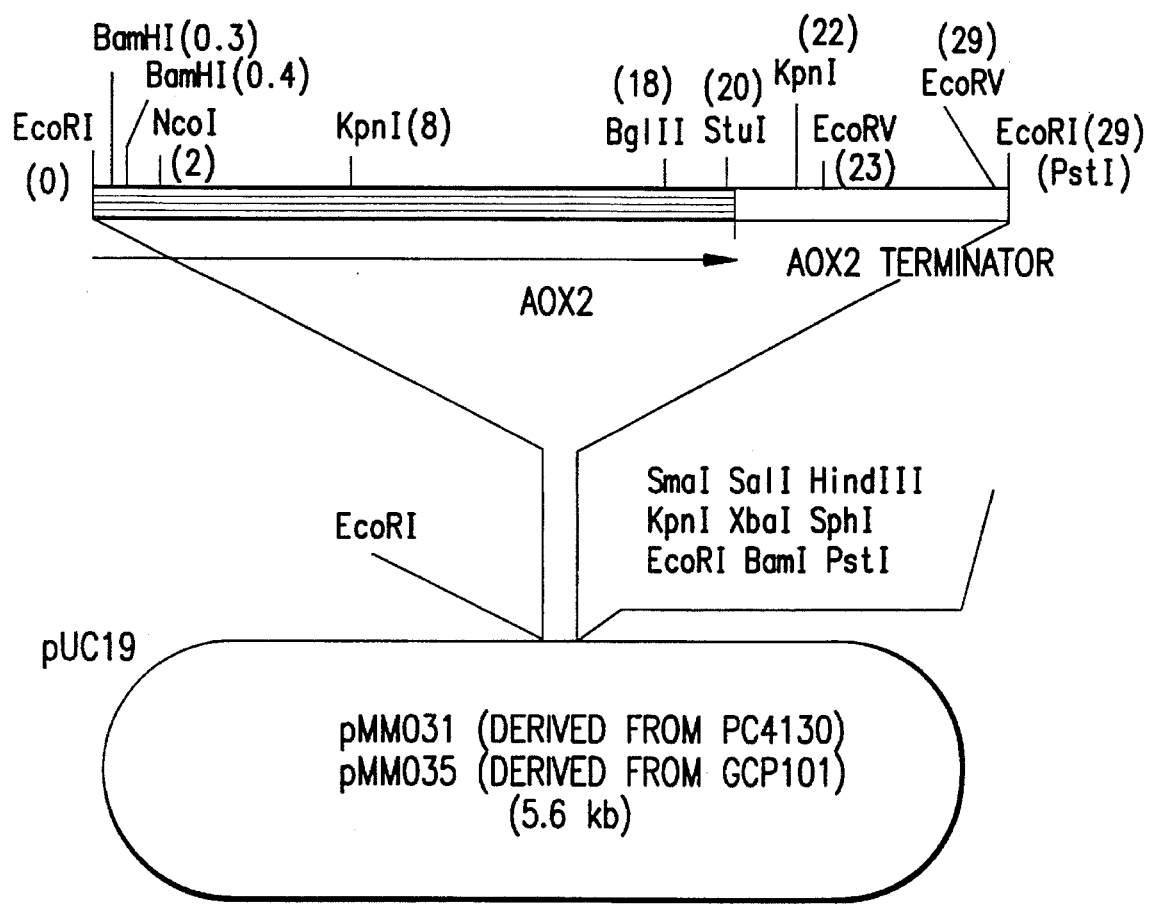
FIG. 4 depicts plasmids pMM031 and pMM035 in which the AOX2 structural gene has been cloned, each with a restriction enzyme map. The numbers in parentheses respectively indicate the distances (×100 bases) from the EcoRI site (distance 0).

The plasmids containing the PC4130-derived AOX2 promoter region and AOX2 structural gene, respectively, were named pMM030 and pMM031, respectively, while the plasmids containing the GCP101-derived AOX2 promoter region and AOX2 structural gene, respectively, were named pMM034 and pMM035, respectively (cf. FIG. 3 and FIG. 4). The sizes of the fragments resulting from digestion of those plasmids with various restriction enzymes were in agreement with the patterns already reported.

EXAMPLE 3 Determination of the Base Sequence of the AOX2 Promoter Region pMM030 and pMM034 were digested with ECORI and each 1.5-kb fragment was recovered and terminally blunted using a DNA blunting kit (Takara Shuzo). Separately, pUC19 was digested with XbaI and, after treatment with mung bean nuclease (Takara Shuzo), ligated to the alkaline phosphatase-treated fragment. Plasmid DNA was prepared from the corresponding transformant. The procedure resulted in subcloning of the PC4130-derived AOX2 promoter region DNA and the GCP101-derived AOX2 promoter region DNA in the XbaI site of pUC19.

From each of those plasmids, 5 or 6 deletion mutant clones differing in insert size by 150 to 300 bp were prepared using a deletion kit for kilosequencing (Takara Shuzo). The deletion mutants were sequenced using a M13 dideoxy sequencing kit (Takara Shuzo). As a result, the 1.5 kb-long base sequence of the PC4130-derived AOX2 promoter region as occurring from ATG and that of the GCP101-derived AOX2 promoter region were wholly determined.

Comparison of the sequences derived from both strains revealed that while, in the PC4130-derived AOX2 structural gene, the nucleotide 255 bp upstream from the initiation codon ATG [in SEQ ID NO: 1, the 1529th to 1531st nucleotides (not shown) following the 1528th nucleotide], namely nucleotide No. 274 in SEQ ID NO: 1, is T, the corresponding nucleotide (No. 274 nucleotide in SEQ ID NO: 3) is C in the GCP101-derived clone, a difference of one base.

EXAMPLE 4

Exchange of the GCP101-Derived AOX2 Promoter for the PC4130-Derived AOX2 Promoter and Vice Versa (cf. EP-A-127304 (JP-A-60-41488))

Figure 5:
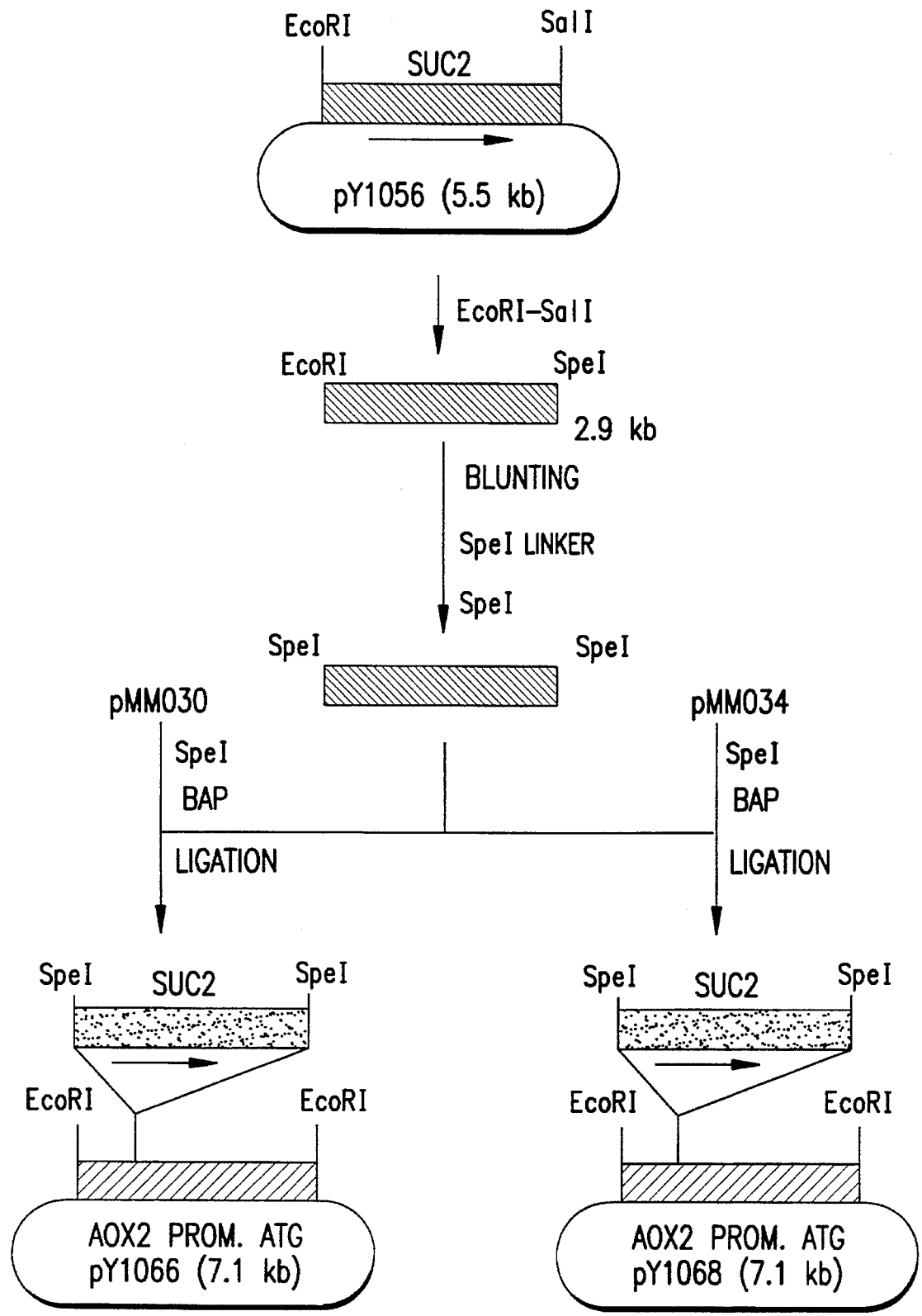
FIG. 5 illustrates the construction of integration vectors, pYI066 and pYI068, for causing transformation in the AOX2 promoter sequence.

Plasmids for AOX2 promoter exchange were constructed by inserting the yeast-derived invertase (SUC2) gene into pMM030 and pMM034 at the SpeI site. Thus, pMM030 and pMM034 each were digested with SpeI and, after alkaline phosphatase treatment, a 4.2-kb fragment was recovered. The plasmid pYI056 derived from pUC19 by cloning the SUC2 gene therein was digested with EcoRI and SalI, fragments were rendered blunt-ended using a DNA blunting kit (Takara Shuzo) and the SpeI linker d(pG-A-C-T-A-G-T-C) (NEB) was ligated thereto using a DNA ligation kit (Takara Shuzo). Then, digestion was performed with SpeI and a 2.9-kb fragment was recovered and ligated to the pMM030- or pMM034derived fragment. Thus were constructed a plasmid, pYI066, containing SUC2 in the region upstream from the PC4130-derived AOX2 promoter and a plasmid, pYI068, containing SUC2 in the region upstream from the GCP101-derived AOX2 promoter (cf. FIG. 5).

The two plasmids were used to transform PC4130 and GCP101 as the hosts. Digestion of each of the plasmids with EcoRI yielded a 4.4-kb fragment. Since regions homologous to the AOX2 promoter region are present on both sides of SUC2, it is expected that when the fragments are introduced into *Pichia pastoris*, homologous recombination would occur in the AOX2 gene promoter region resulting in mutual exchange of the AOX2 promoters derived from both strains.

*Pichia pastoris* was transformed with reference to the method of Cregg et al. [Mol. Cell. Biol., 5, 3376–3385 (1985)]. Thus, PC4130 and GCP101 were cultured overnight in 5 mL of YPD medium at 30° C. and then used for inoculation (0.01%). After 16 to 20 hours of incubation when $A_{600}$ increased from 1 to 5, each culture was transferred to a 50-ml Corning tube and centrifuged. The cells obtained were suspended in 20 ml of sterile water and centrifuged again. The cells thus obtained were suspended in 10 ml of SED buffer (1M sorbitol, 25 mM EDTA and 50 mM dithiothreitol), centrifuged and washed twice with 1M sorbitol solution.

They then were suspended in 10 ml of a Zymolyase solution (prepared by dissolving Zymolyase 100T in SED buffer to a concentration of 50 µg/ml) and incubated at 30° C. for 30 minutes. Microscopic observation confirmed the possibility of cell disruption upon addition of 10% SDS in an amount of ⅒ volume. Cells were collected by centrifugation, washed with two portion of 1M sorbitol solution and suspended in CaS buffer (1M sorbitol and 10 mM calcium chloride), followed by centrifugation. The cells recovered were suspended in 1 ml of CaS buffer and 100 µl of the resultant spheroplast suspension was transferred to a polypropylene tube.

Thereto were added 10 µg each of the 4.4-kb DNA fragments obtained by EcoRI digestion of pYI066 and pYI068 and the mixture was allowed to stand at room temperature for 20 minutes. Then, 1 ml of PEG solution (20% polyethylene glycol 3350, 10 mM calcium chloride and 10 mM Tris base, pH 7.4) was added and the resultant mixture was allowed to stand at room temperature for 15 minutes. Cells were collected by centrifugation, suspended in 150 µL of SOS solution (1M sorbitol, 10 mM calcium chloride and 0.3×YPD) and allowed to stand at room temperature for 30 minutes. After addition of 850 μL of 1M sorbitol, 10, 100 and 500 μl of the resultant spheroplast suspension respectively were added to 10-ml portions of top agar (1M sorbitol, 1.35% yeast nitrogen base without amino acids, 400 μg/l biotin, 2% glucose and 1% agar) and, after stirring, each suspension was spread over bottom plates (identical in composition to the top agar, solidified on dishes).

Incubation was carried out at 30° C. for 4 days. The top agar layers, if covered with the fungus, each were scraped off using a sterile drug spoon and filtered through a 3G1 glass filter for removing the agar. An appropriate amount of each fungal cell-containing filtrate was diluted and used for inoculation onto MSu plates (0.7% yeast nitrogen base without amino acids 400 μg/l biotin, 0.5% saccharose and 1% agar powder). One of the resultant single colonies was chosen and suspended in sterile water and used for further inoculation.

A relatively large single colony was inoculated onto 2% MeOH-YNB w/o a.a. plates and, after a lapse of 5 days, judgment was made as to proliferation (Mut$^+$) or no proliferation (Mut$^-$). As seen in Table 2, 20% of the transformants derived from PC4130 (Mut$^-$ strain) by introduction of pYI068 (mutant type AOX2 promoter) thereinto grew on the above kind of plate. Conversely, 6% of the transformants derived from GCP101 (Mut$^+$ strain) by introduction of pYI066 (natural type AOX2 promoter) could not grow on said kind of plate.

Thus, the exchange of the mutant AOX2 promoter for the natural AOX2 promoter resulted in increased promoter activity, leading to conversion of the Mut$^-$ strain to a Mut$^+$ strain.

TABLE 2

| Host | Percentage of Mut$^+$ strains | |
|---|---|---|
| | Plasmid introduced | |
| | pYI066 (PC4130-derived) (natural AOX2 promoter) | pYI068 (GCP101-derived) (mutant AOX2 promoter) |
| PC4130 (Mut$^-$) | 0% | 20% |
| GCP101 (Mut$^+$) | 94% | 100% |

EXAMPLE 5

Search for the Location of Mutation in the AOX2 Promoter in Other Mut$^+$ Transformants The HSA-producing *Pichia pastoris* PC4105 strain is a strain derived from the *Pichia pastoris* GTS115 strain by substitution of the HSA expression plasmid pPGS1 for the AOX1 region practicing the methods described above. The difference between pPGS1 and pPGP1 of Example 1 lies only in that the poly-A region occurring on the 3' side of HSA in pPGP1 is missing in pPGS1.

Figure 6:
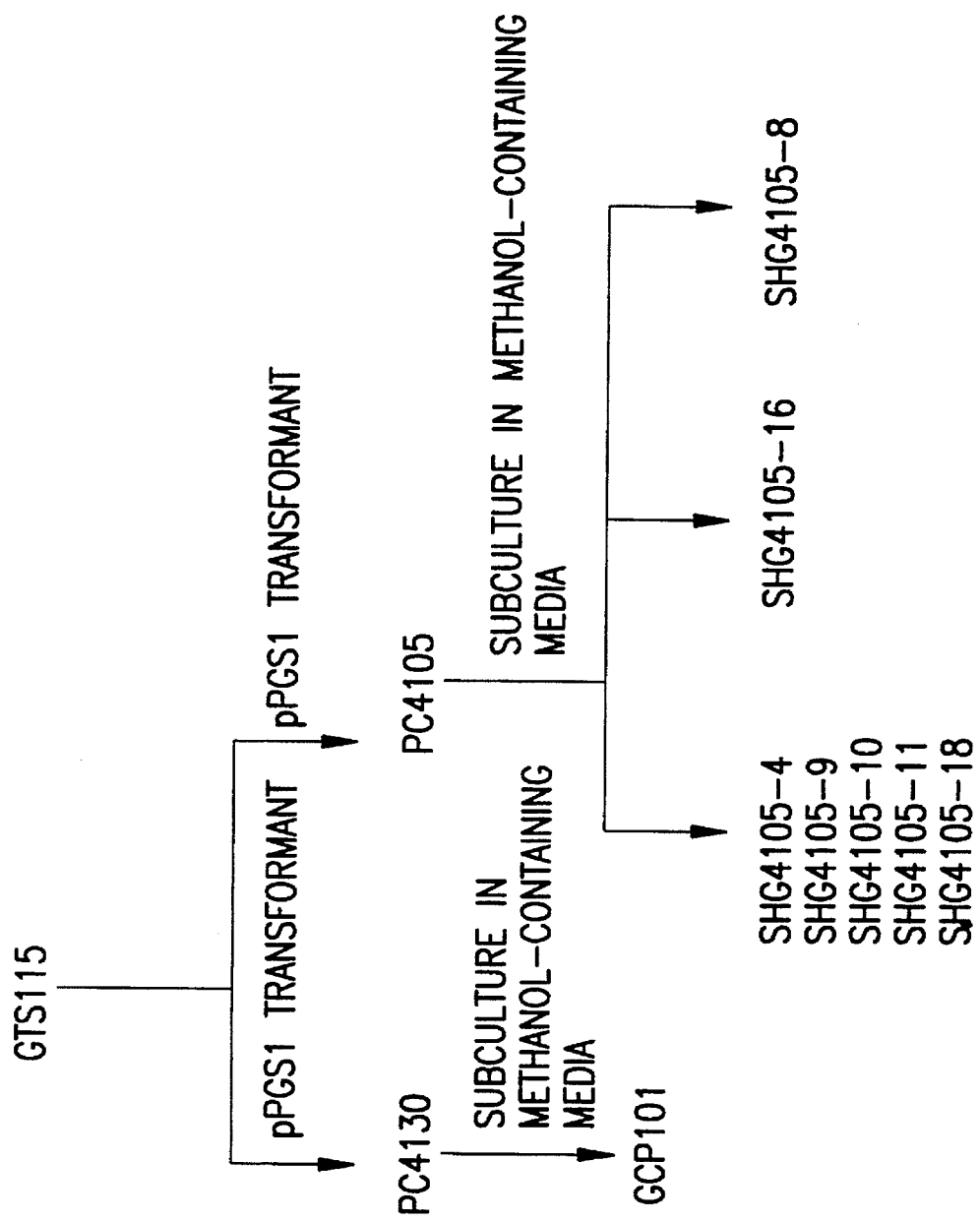
FIG. 6 shows the process for obtaining each strain having a mutant AOX2 promoter.

For the PC4105 strain, the same subculture experiment as Example 1 was performed using 7 independent flasks. As a result, all the seven flasks gave strains (Mut$^+$ strains) showing improved proliferation in the methanol-containing medium. The single colonies respectively isolated were designated as SHG4105-4, SHG4105-8, SHG4105-9, SHG4105-10, SHG4105-11, SHG4105-16 and SHG4105-18, respectively (cf. FIG. 6).

The chromosomal DNA's were extracted and purified from the 7 strains and from PC4105 by the method of Cameron et al. [Nucleic Acids Res.,4, 1429 (1977)]. Together with the chromosomal DNA's from both the strains PC4130 and GCP101 obtained in Example 2, the DNA's were subjected to AOX2 promoter region DNA amplification by the PCR method. (Thus, primers first were synthesized. Based on the base sequence (SEQ ID NO: 1) determined in Example 3, the counter strand sequence corresponding to the bases occurring 143 bases to 160 bases upstream from ATG of the AOX2 gene, namely base No. 1369 to base No. 1386 in SEQ ID NO: 1, with an EcoRI site joined thereto, was used as a primer for the 3' side (SEQ ID NO: 5) and the main strand sequence corresponding to the bases occurring 786 bases to 803 bases upstream from said ATG, namely base No. 726 to base No. 733 in SEQ ID NO: 1, with a BamHI site joined thereto, was used as a primer for the 5' side (SEQ ID NO: 6). The above two sequences were synthesized by the phosphoamidite method using an Applied Biosystems model 381A DNA synthesizer.)

For the above-mentioned 10 chromosomal DNA's, in which each was used as a template, PCR was performed using the two primers and proceeding as described in the explanatory note attached to Takara Shuzo's GeneAmp™ kit. For the reaction (PCR), a Perkin Elmer-Cetus mode PJ2000 DNA thermal circular apparatus was used and the cycle comprising 1 minute of thermal denaturation of DNA strand at 94° C., 2 minutes of annealing with the primers at 37° C. and 2 minutes of polymerase-catalyzed chain extension at 72° C. was repeated 35 times. After agarose gel electrophoresis, a DNA of about 650 bp in size was recovered and purified using SUPREC™-01 (Takara Shuzo).

For SHG4105-16, a DNA of about 250 bp in size was amplified, hence the DNA was recovered and purified. Separately, pUC19 was digested with EcoRI and BamHI and a 2.7-kb fragment was recovered and subjected to alkaline phosphatase treatment. That fragment then was ligated to each amplified DNA, the ligation mixture was used to transform the *E. coli* competent cell strain DH5 (Toyobo) and a transformant strain carrying the contemplated plasmid was selected from among the transformants obtained. Plasmid DNA was prepared by the alkali-SDS method. The DNA's of the 10 plasmids thus prepared were subjected to sequencing of about 200 bases from the EcoRI site using a M13 dideoxy sequencing kit (Takara Shuzo).

As regards SHG4105-16, the entire base sequence amplified was determined. PC4130 and PC4105 gave the same base sequence as SEQ ID NO: 1 as already reported [Koutz et al., Yeast, 5, 167–177 (1989)]. As for GCP101, the mutation from T to C at the site 255 bp upstream from ATG as found in Example 3 was confirmed (SEQ ID NO: 3). As regards SHG4105-4, SHG4105-9, SHG4105-10, SHG4105-11 and SHG4105-18, the same mutation as in GCP101 was revealed with the promoter sequence of SEQ ID NO: 3. In SHG4105-8, the nucleotide T 255 bp upstream from ATG remained unchanged but insertion of a 19-base repeating sequence shown under SEQ ID NO: 7 was found between the GGAGA sequences at the sites about 215 bp and about 234 bp upstream from ATG [giving the promoter sequence shown under SEQ ID NO: 4 as resulting from addition of SEQ ID NO: 7 to SEQ ID NO: 1 between base No. 1314 (A) and base No. 1315 (C)]. In SHG4105-16, the T 255 bp upstream from ATG was retained but deletion of a 439-bp region 342 bp to 780 bp upstream from ATG [base No. 749 (C) to base No. 1187 (T) in SEQ ID NO: 1] was found (SEQ ID NO: 2).

EXAMPLE 6

Activity of the GCP101-Derived AOX2 Promoter

Vectors for the expression of HSA under the control of the GCP101-derived AOX2 promoter or the PC4130-derived AOX2 promoter were constructed for confirming the promoter activity thereof.

Figure 7:
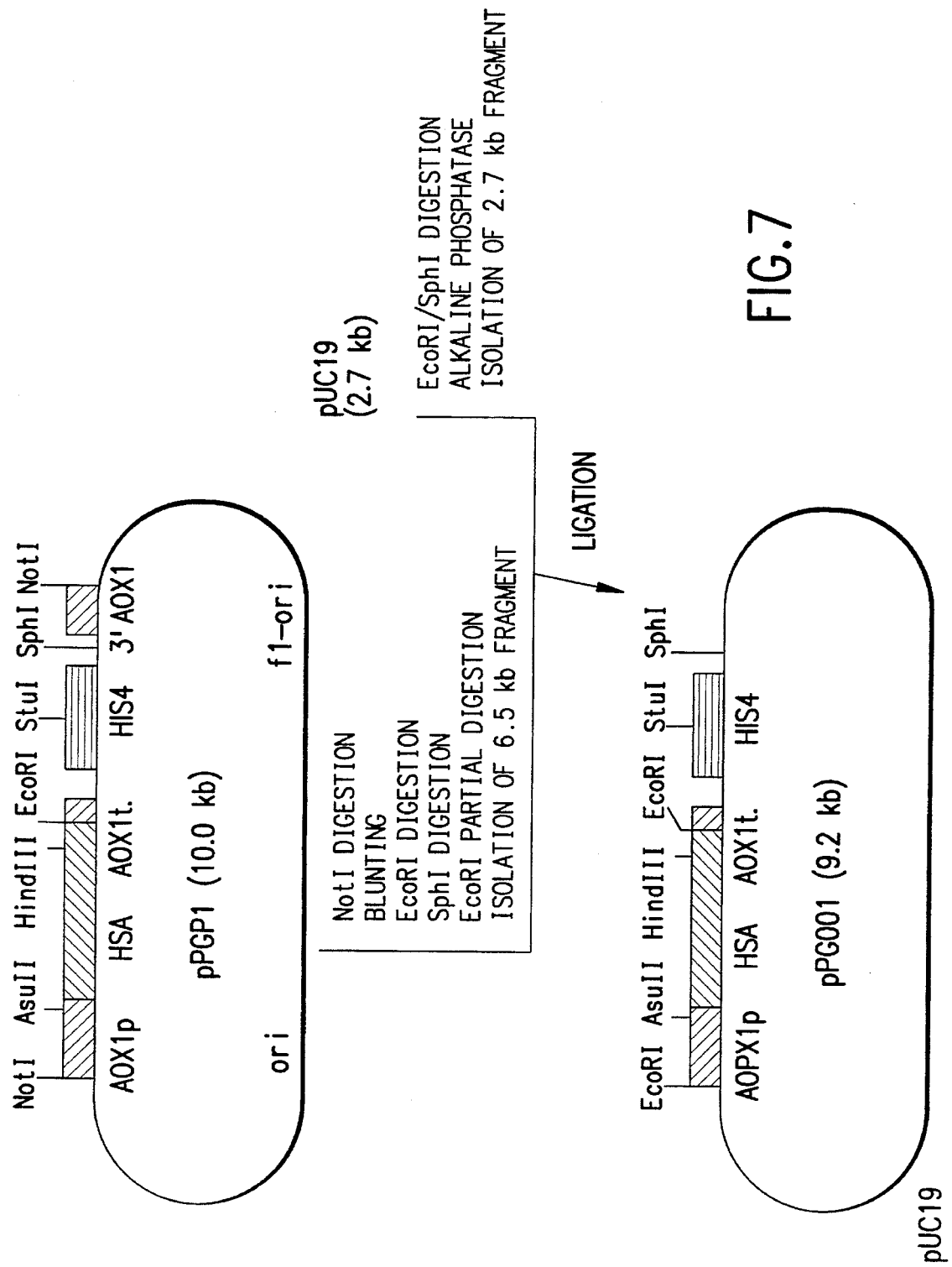
FIG. 7 illustrates the construction of pPG001.

Thus, pPGP1 was digested with NotI and rendered blunt-ended using a DNA blunting kit (Takara Shuzo)o Thereto was ligated the EcoRI linker d(pG-G-A-A-T-T-C-C) (Takara Shuzo). Following complete digestion with SphI and partial digestion with EcoRI, a 6.5-kb fragment was recovered and purified. pUC19 was digested with EcoRI and SphI and the digest was subjected to alkaline phosphatase treatment. The vector mixture was ligated to the above-mentioned 6.5-kb fragment to yield a pUC19-derived plasmid, pPG001, allowing expression of HSA under the control of the AOXI promoter and having HIS4 as a selective marker (cf. FIG. 7).

pPG001 was digested partially with EcoRI and rendered blunt-ended using a DNA blunting kit (Takara Shuzo). Separately, a BamHI linker having the sequence GGGATCCC was synthesized by the phosphoamidite method using an Applied Biosystems model 381A DNA synthesizer. The linker was phosphorylated using T4 polynucleotide kinase (Takara Shuzo) and subjected to ligation with the blunt-ended fragment mentioned above. Following digestion with AsuII and BamHI, a 7.1-kb fragment was purified. Separately, pPGP1 was digested with HindIII and rendered blunt-ended using a DNA blunting kit (Takara Shuzo). Thereto was ligated the BamHI linker d(pG-G-G-A-T-C-C-C) and, following digestion with AsuII and BamHI, a 1.9-kb fragment was purified. Ligation of that fragment to the 7.1-kb fragment mentioned above gave a plasmid named pPG002.

pMM030 and pMM034 each were digested with EaeI, and a 1.5-kb fragment was recovered and rendered blunt-ended by treatment with mung bean nuclease (Takara Shuzo). An AsuII linker having the sequence CTTCGAAG was synthesized by the phosphoamidite method using an Applied Biosystems model 381A DNA synthesizer, phosphorylated using T4 polynucleotide kinase (Takara Shuzo) and ligated to each blunt-ended fragment mentioned above. Following digestion with EcoRI and AsuII, a 1.5-kb AOX2 promoter region fragment was recovered.

Figure 8:
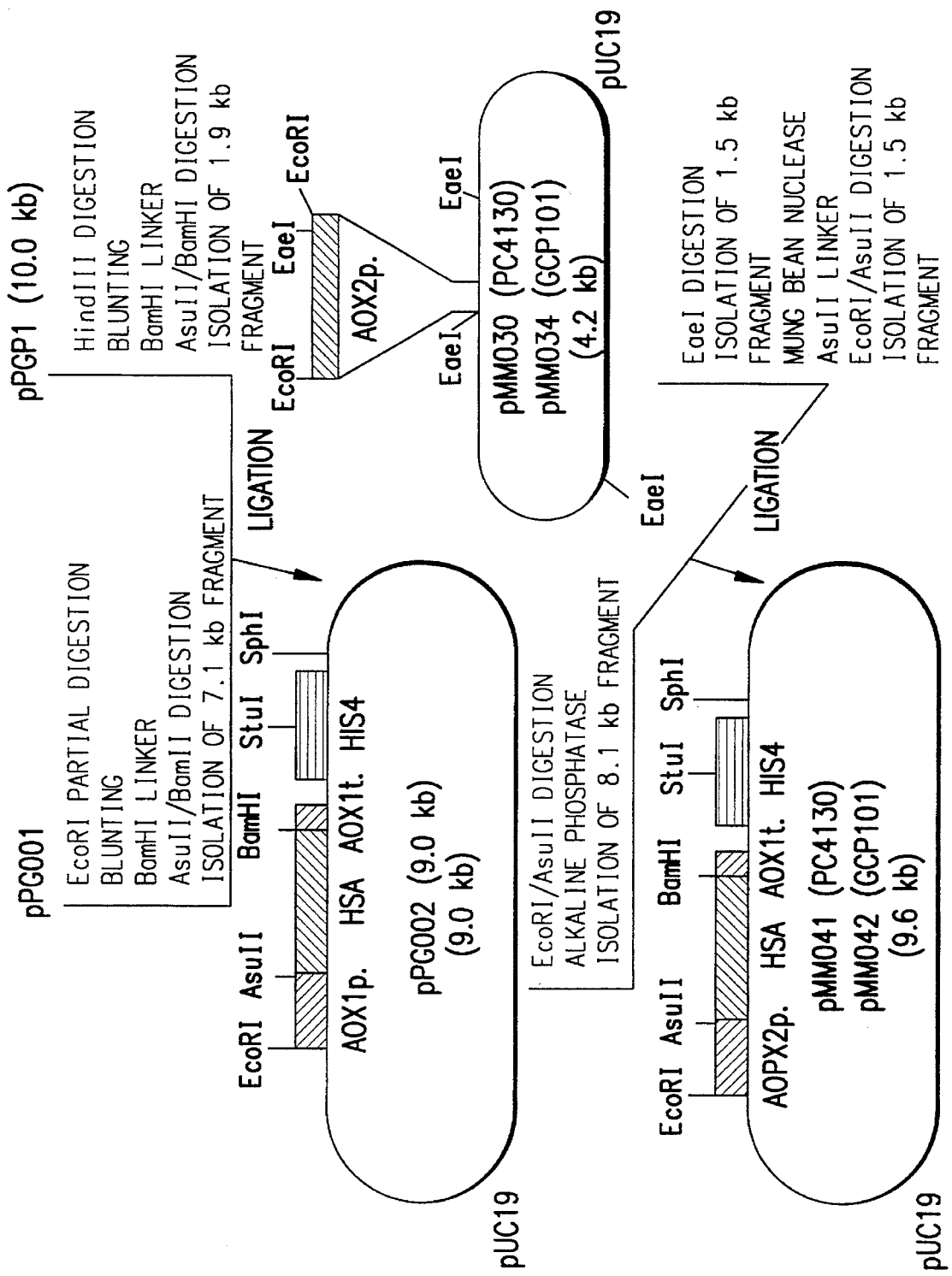
FIG. 8 illustrates the construction of plasmids, pMM041 and pMM042, allowing expression of HSA under the control of the AOX2 promoter.

Separately, the plasmid pPG002 allowing expression of HSA under the control of the AOX1 promoter and having the HIS4 region was digested with EcoRI and AsuII, and a 8.1-kb fragment lacking the AOX1 promoter region was recovered following alkaline phosphatase treatment. That fragment was ligated to the 1.5-kb AOX2 promoter region fragment. Thus, a plasmid, pMM041, allowing HSA expression under the control of the PC4130-derived (natural) AOX2 promoter and a plasmid, pMM042, allowing HSA expression under the control of the GCP101-derived (mutant) AOX2 promoter were constructed (cf. FIG. 8).

pPG002, pMM041 and pMM042 each were linearized by digestion with the enzyme StuI, cleaving the plasmids at the single cleavage site in the HIS4 region, and introduced into GTS115. The plasmids integrated into GTS115 in the his4 region as a result of homologous recombination. *Pichia pastoris* was transformed in the same manner as in Example 5.

Because the plates used were histidine-requiring, all colonies formed after transformation were considered to be transformant colonies. The agar was removed by filtration through a 3G1 glass filter and a portion of each filtrate was inoculated into YPD medium. After overnight incubation at 30° C., the culture broth was distributed into various media (50 mL) to give an initial $A_{540}$ of 0.1. Samples were taken from each culture broth at 24-hour intervals and assayed for human serum albumin concentration in the culture supernatant by the RPHA method (European Patent No. 122620).

It was found that, while the human serum albumin-producing activity was low with the PC4130-derived AOX2 promoter, the GCP101-derived AOX2 promoter was comparable in human serum albumin production-inducing activity to the AOX1 promoter. The results are shown in Table 3.

TABLE 3

| | HSA production (mg/L) in the culture supernatant | | | |
|---|---|---|---|---|
| | | Cultivation time (hours) | | |
| Strain | Medium | 24 | 48 | 120 |
| pPG002/GTS115 | 2% MeOH—YP | 8 | 30 | 40 |
| (AOX1 promoter) | 4% MeOH—YP | 2 | 60 | 120 |
| pMM041/GTS115 | 2% MeOH—YP | — | — | 1 |
| (PC4130-derived natural AOX2 promoter) | 4% MeOH—YP | — | 1 | 1 |
| pMM042/GTS115 | 2% MeOH—YP | 8 | 20 | 40 |
| (PCP101-derived mutant AOX2 promoter) | 4% MeOH—YP | 1 | 60 | 120 |

—: Undetectable

EXAMPLE 7

HSA Producer Preparation Using the Mutant AOX2 Promoter pMM042 was digested with StuI and introduced into the GTS115 strain, as in Example 6. While integration is effected through homologous recombination with the his4 region of the GTS115 strain, in some instances one transformation procedure may result in integration of two or more copies. Each colony that had formed after transformation was collected by removing the agar by filtration through a 3G1 glass filter, the filtrate was diluted with sterile water to give a concentration of 100 cells/plate and the dilution was spread over YNB w/o a.a. plates (0.7% yeast nitrogen base without amino acids, 2% glucose and 1.5% agar powder). Incubation was carried out at 30° C. for 3 days for single colony formation.

The chromosomal DNA was extracted from each of the thus-obtained 10 clones in the same manner as in Example 2. Southern analysis [Southern, E. M., J. Mol. Biol., 98, 503 (1975)] was performed using the Pichia-derived chromosomal HIS4 region as a probe and the number of copies of pMM042 that had been integrated was determined. Thus, 5 µg of each chromosomal DNA was digested with BglII and subjected to agarose gel electrophoresis. The gel was treated with 0.2 N HCl for 30 minutes, transferred to an alkaline denaturing solution (0.2 N NaOH and 0.6M NaCl) and, after 30 minutes of reaction, transferred to a neutralizing solution [0.2M Tris (pH 7.4), 0.6M NaCl]. The neutralization treatment (30 minutes) was conducted twice. Blotting was performed to Hybond-N (Amersham) in a conventional manner.

A KpnI fragment (0.6 kb) of *Pichia pastoris* HIS4 was labeled for use as probe. Probe preparation, hybridization and washing were carried out using a DNA labeling and detection kit for DIG-ELISA (Boehringer Mannheim-Yamanouchi) and following the brochure attached thereto. With GTS 115, a 2.7-kb band should occur because it has a 2.7-kb HIS4 region, as shown in FIG. 9-(a). Integration of one copy of pMM042 into the his4 region of GTS115 would result in appearance of a 7.8-kb band and a 4.5-kb band.

Integration of 2 copies of pMM042 in the same manners would result in appearance of a further 9.6-kb band in addition to the 7.8-kb and 4.5-kb bands. Integration of 3 copies would result in the 7.8-kb and 4.5-kb bands as well as the 9.6-kb band with a doubled density. Integration of 4 copies would result in the same molecular weight bands but with a tripled density.

pMM042 was found to have been integrated into GTS115 in the his4 region. Strains varying in pMM042 copy number from 1 to 4 were obtained. Among them, one of the strains resulting from integration of one copy was designated as UHG42-15, one of the strains resulting from integration of 2 copies as UHG42-3 and one of the strains resulting from integration of 3 copies as UHG42-12 [FIG. 9-(b) to (d)].

UHG42-15, UHG42-3 and UHG42-12 were evaluated for HSA productivity after separation into clones. They were inoculated into YPD medium and cultured overnight at 30° C. Each culture broth was inoculated into 50 mL of 2% MeOH-YP medium to an initial $OD_{540}$ of 1. Culture broth samples were taken at 24-hour intervals and the concentration of human serum albumin in each culture supernatant was determined by the RPHA method (European Patent No. 122620).

As shown in Table 4, a maximum HSA production of 80 mg/l was obtained with UHG42-15; 100 mg/l with UHG42-3; and 160 mg/l with UHG42-12. Thus, highly productive strains were obtained by cloning, with the productivity increasing with the increasing number of copies. In other words, strains capable of high production of HSA could be obtained using the plasmid pMM042 causing HSA expression using the GCP101-derived (mutant) AOX2 promoter.

TABLE 4

| | HSA production levels in the culture supernatants for some clones (mg/l) | | |
|---|---|---|---|
| | Cultivation time (hours) | | |
| Strain | 24 | 48 | 72 |
| UHG42-15 (one copy) | 15 | 80 | 80 |
| UHG42-3 (2 copies) | 30 | 100 | 100 |
| UHG42-12 (3 copies) | 40 | 160 | 160 |

The mutant AOX2 promoter obtained in accordance with the invention has a markedly increased promoter activity as compared with the natural (wild type) promoter. By using such a mutant promoter, it is now possible to cause expression of heterologous proteins in large quantities. Therefore, the subject matter of the invention is believed to have importance as a novel expression system in the field of genetic engineering.

All references appearing herein are incorporated by reference in their entirety.

While the invention has been described in detail and with reference to specific examples thereof, it will be apparent to one skilled in the art that various changes and modifications can be made therein without departing from the spirit and scope thereof.

What is claimed is:

1. A mutant *Pichia pastoris* AOX2 promoter consisting of the natural AOX2 promoter of SEQ ID NO: 1 comprising at least one of the following mutations:
    (i) a deletion of the bases from 749 to 1187, inclusive;
    (ii) a substitution of C for base 1274; or
    (iii) an insertion of SEQ ID NO: 7 between bases 1314 and 1315.

2. A plasmid comprising the mutant AOX2 promoter of claim 1.

3. The plasmid of claim 2, wherein said plasmid is an expression plasmid comprising a nucleic acid molecule encoding a protein heterologous to *Pichia pastoris* operatively linked in the proper reading frame with said mutant AOX2 promoter.

4. The expression plasmid of claim 3, wherein said nucleic acid molecule encoding a heterologous protein is a gene for human serum albumin.

5. A transformed host cell comprising the plasmid of any one of claims 2, 3, or 4 in a *Pichia pastoris* yeast cell.

6. The mutant AOX2 promoter of claim 1, wherein said promoter is selected from the group consisting of SEQ ID NO: 2, SEQ ID NO: 3 and SEQ ID NO: 4.

7. A *Pichia pastoris* strain carrying, on the chromosome thereof, an AOX2 gene under the control of the mutant AOX2 promoter of claim 1.

8. A method of producing a protein heterologous to *Pichia pastoris* comprising cultivating the transformed host cell of claim 5 in a methanol-containing medium to induce said mutant AOX2 promoter, wherein induction of said mutant AOX2 promoter initiates expressiozn of a nucleic acid molecule encoding said protein operably linked thereto to produce said protein heterologous to *Pichia pastoris*.

* * * * *